US009107356B2

(12) United States Patent
Freeman

(10) Patent No.: US 9,107,356 B2
(45) Date of Patent: Aug. 18, 2015

(54) HYBRID CARROT VARIETY NUN 85931

(71) Applicant: Nunhems B.V., Nunhems (NL)

(72) Inventor: Roger Freeman, Brooks, OR (US)

(73) Assignee: Nunhems B.V., AB Nunhem (NL)

( * ) Notice: Subject to any disclaimer, the term of this patent is extended or adjusted under 35 U.S.C. 154(b) by 0 days.

(21) Appl. No.: 14/267,997

(22) Filed: May 2, 2014

(65) Prior Publication Data

US 2014/0245473 A1    Aug. 28, 2014

(51) Int. Cl.
*A01H 5/06* (2006.01)
*C12Q 1/68* (2006.01)
*A01G 1/00* (2006.01)

(52) U.S. Cl.
CPC ............... *A01H 5/06* (2013.01); *A01G 1/001* (2013.01); *C12Q 1/6895* (2013.01); *C12Q 2600/112* (2013.01)

(58) Field of Classification Search
None
See application file for complete search history.

(56) References Cited

U.S. PATENT DOCUMENTS

2008/0098493 A1 * 4/2008 Maxwell ............... 800/260
2011/0283412 A1 * 11/2011 Stelpflug et al. ....... 800/263

FOREIGN PATENT DOCUMENTS

EP    0534858      3/1993
WO   2008/107097   9/2008

OTHER PUBLICATIONS

Kaeppler et al (2000) Plant Molec. Biol. 43: 179-188.*
Baranski 2008 Genetic Transformation of Carrot (*Daucus carota*) and Other Apiaceae Species, Transgenic Plant Journal (2)1: 18-38.

* cited by examiner

*Primary Examiner* — Medina A Ibrahim
*Assistant Examiner* — Steven Bernacki

(57) ABSTRACT

The present invention relates to plants of a carrot variety NUN 85931 and seeds and progeny thereof. The invention further relates to methods for producing a carrot plant by traditional breeding methods. The invention further relates to a method for producing a carrot plant containing in its genetic material one or more transgenes.

21 Claims, No Drawings

HYBRID CARROT VARIETY NUN 85931

FIELD OF THE INVENTION

The present invention relates to the field of plant breeding. In particular, the invention provides for a new and distinct carrot variety designated NUN 85931 (or "NUN 85931 CAC" or "NUN 85931 carrot" or "85931" or NUN 85931 hybrid or 85931 F1 or NUN 85931 F1).

BACKGROUND OF THE INVENTION

Carrot is a biennial plant that grows a rosette of leaves in the spring and summer, while building up the stout taproot, which stores large amounts of sugars for the plant to flower in the second year. The flowering stem grows several decimeters (e.g. 60-200 cm) tall, with an umbel of white flowers that produce a fruit called a mericarp.

Carrot (*Daucus carota* subsp. *sativus*), is a root vegetable, usually orange in color, though purple, red, white, cream, and yellow varieties exist. It has a crisp texture when fresh. The most commonly eaten part of a carrot is a root, although the greens are edible as well. It is a domesticated form of the wild carrot *Daucus carota*, native to Europe and southwestern Asia. The domestic carrot has been selectively bred for its greatly enlarged and more palatable, less woody-textured edible taproot. The world production of carrots and turnips for calendar year 2011 was almost 35.658 million tonnes (Food and Agriculture Organization of the United Nations (FAO)).

Vegetable breeder's aim is to combine desirable traits in a single variety. Such desirable traits may include any trait deemed beneficial by a grower and/or consumer, including greater yield, resistance to insects, disease or other pests, tolerance to environmental stress, enhanced growth rate and nutritional value.

A uniform population of a breeding line can be obtained by self-pollination and selection for type. Plants thus obtained become homozygous at almost all gene loci, i.e. a homozygous plant. Crossing two such plants of different genotypes produces a uniform population of hybrid plants that are heterozygous for many loci. On the other hand, a cross of two plants each heterozygous at a number of loci produces a population of plants that differ genetically and are not uniform. Due to this non-uniformity, performance of such plants is unpredictable.

Breeders thus prefer development of homozygous inbred plant that can be crossed to produce uniform varieties. Pedigree breeding and recurrent selection are examples of breeding methods that have been used to develop inbred plants from breeding populations. Those breeding methods combine the genetic backgrounds from two or more plants or various other broad-based sources into breeding pools from which new lines and hybrids derived therefrom are developed by selfing and selection of desired phenotypes. The new lines and hybrids are evaluated to determine which of those have commercial potential.

So far, breeding efforts have provided a number of useful carrot lines with beneficial traits, however, there remains a great need in the art for new lines with further improved traits. There is thus a need for new carrot varieties having specific combination of trait or color.

SUMMARY OF THE INVENTION

The objective of the invention was to develop an Peeler type variety with a cream skin. The present invention provides seed of a new cream carrot (*Daucus carota*) variety, designated NUN 85931, having been deposited under Accession Number NCIMB 42390, a plant, or a part thereof, produced by growing said seed. The invention also provides methods and compositions relating to plants, plant parts, seeds and progenies of carrot variety NUN 85931.

Variety NUN 85931 is most similar to comparison variety PS 1441. However, NUN 85931 differs from PS 1441 in one or more, e.g., at least two, at least three, optionally all morphological and/or physiological characteristics (measured at market maturity/harvest stage) listed in the following (see also Table 1), when grown under the same environmental conditions:
  a (average) carrot length (minus taproot) that is at least about 10%, or preferably at least about 14%, 17%, 20%, 23% or even about 26% longer than carrot length of PS 1441;
  a (average) leaf petiole length that is at least about 15%, or preferably at least about 20%, 22.5%, 25%, 27.5%, 30% or even about 33% longer than the leaf petiole length of PS 1441;
  a (average) plant top height that is at least about 5%, or preferably at least about 10%, 12.5%, 15%, 16%, 17%, or even about 18.2% higher than the plant top height of PS 1441;
  a (average) plant top neck diameter that is at least about 5%, or preferably at least about 7.5%, 10%, 12.5%, 15%, 16% or even about 16.7% larger than the plant top neck diameter of PS 1441;
  a root with no secondary root scars, which are not prominent, rather than a surface that has a few prominent secondary root scars as in PS 1441.

Other differences between variety NUN 85931 CAC and PS 1441 reveals that NUN 85931 CAC also differs significantly from PS 1441 in one or more, e.g., at least two, at least three, optionally all morphological and/or physiological characteristics listed in the following (see also Table 1), when grown under the same environmental conditions:
  leaf blade divisions that are medium rather than fine as in PS 1441;
  petiole pubescence that is present rather than slightly present/absent as in PS 1441.

The present invention provides a carrot plant variety designated NUN 85931, representative seed of said variety having been deposited under NCIMB Accession Number 42390, and plant parts of the new variety such as for example seed, leaf, pollen, an ovule, taproot, root and a cell of the plant.

The invention also concerns the seed of hybrid carrot NUN 85931, representative seed of said variety having been deposited under Accession Number NCIMB 42390, a plant, or a part thereof, produced by growing said seed, or carrot plants having all or essentially all the physiological and morphological characteristics of NUN 85931.

The invention further relates to breeding methods using plants or seed of carrot variety NUN 85931.

Other objects, features and advantages of the present invention will become apparent from the following detailed description. It should be understood, however, that the detailed description and any specific examples provided, while indicating specific embodiments of the invention, are given by way of illustration only, since various changes and modifications within the spirit and scope of the invention will become apparent to those skilled in the art from this detailed description.

DETAILED DESCRIPTION OF THE INVENTION

The present invention provides a carrot plant variety designated NUN 85931, representative seed of said variety having been deposited under NCIMB Accession Number 42390, and plant parts of the new variety such as for example seed, leaf, pollen, an ovule, taproot, root and a cell of the plant. In another aspect, the plant parts include leaf, pollen, an ovule, taproot, root and a cell of the plant. In yet another aspect, the plant part is a root. Also provided are carrot plants having all or essentially all the physiological and morphological characteristics of such a plant, i.e. a carrot plant that does not differ (statistically) significantly from NUN 85931 in the morphological and/or physiological characteristics of Table 1, when grown under the same conditions.

The invention also concerns the seed of hybrid carrot NUN 85931, representative seed of said variety having been deposited under Accession Number NCIMB 42390, a plant, or a part thereof, produced by growing said seed. In another aspect, the invention relates to carrot plants having all or essentially all the physiological and morphological characteristics of NUN 85931 when grown under the same conditions. The carrot seed of the invention (i.e. seed from which a plant of variety NUN 85931 can be grown) may be provided as an essentially homogeneous population of carrot seed according to the invention. Essentially homogeneous populations of seed are generally free from substantial numbers of other seed. Therefore, seed of hybrid NUN 85931 or carrot plants having all or essentially all the physiological and morphological characteristics of NUN 85931 may be defined as forming at least about 97% of the total seed, including at least about 98%, 99% or more of the seed. The seed population may be separately grown to provide an essentially homogeneous population of carrot plants according to the invention. Also provided are plants or plant parts such as seed (produced on the plant NUN 85931, e.g. after self-pollination or cross-pollination by another carrot plant), leaf, pollen, an ovule, taproot, roots or a cell produced by growing the seeds of the invention. In yet another aspect, the plant part is a root.

In another aspect the invention relates to an Essentially Derived Variety of NUN 85931 having at least one, two or three physiological and/or morphological characteristics which are (statistically significantly) different from those of NUN 85931 and which otherwise has essentially all physiological and morphological characteristics of a carrot plant designated NUN 85931, a representative sample of seeds of which having been deposited under Accession Number NCIMB 42390.

In another aspect, the invention relates to an Essentially Derived Variety of NUN 85931 having at least one or two physiological and/or morphological characteristics which are significantly different from those of NUN 85931 and which otherwise comprises at least 3, 4 or 5 or more (or all) of the distinguishing characteristics 1)-5), or preferably at least 3, 4, 5, 6, 7, or all 8 of the distinguishing characteristics 1)-10) of NUN 85931 and/or has essentially all physiological and morphological characteristics of a carrot plant designated NUN 85931 obtainable by selecting a natural or induced mutant, or a somaclonal variant from a population of plants designated NUN 85931.

In still another aspect, a carrot plant, or a part thereof, is provided which does not significantly differ in distinguishing characteristics 1)-4) of carrot plant NUN 85931 when grown under the same conditions. In yet another aspect, the invention relates to a carrot plant, or a part thereof, which does not significantly differ in distinguishing characteristics 1)-4) and additionally comprises (i.e. does not differ statistically significantly in) at least one, two, three or all of distinguishing characteristics 5)-8) of carrot plant NUN 85931 when grown under the same conditions.

In yet another aspect, the invention relates to a carrot plant, or a part thereof, which does not differ significantly from carrot plant NUN 85931 in any of the physiological and morphological characteristics of Table 1 when grown under the same conditions.

In another aspect the invention relates to a carrot plant, or a part thereof, which does not significantly differ from carrot plant NUN 85931 in any of the distinguishing characteristics consisting (measured at market maturity/harvest stage, see USDA descriptor) of 1) average carrot length (minus taproot), 2) average leaf petiole length from crown to first pinna, 3) average plant top height (from shoulder to top of crown), and 4) average plant top neck diameter. In another embodiment, the carrot plant of the invention additionally does not significantly differ from carrot plant NUN 85931 in in any of the distinguishing characteristics consisting (measured at market maturity/harvest stage) of 5) number and prominence of secondary root scars, 6) leaf blade divisions, 7) petiole pubescence and 8) below ground exterior color.

In still another aspect, a carrot plant is provided, which statistically significantly differs from NUN 85931 in at least one morphological and/or physiological characteristic, but which does not differ significantly from NUN 85931 in the following characteristics (see USDA descriptor) when grown under the same conditions (measured at market maturity): and 5) number and prominence of secondary root scars 6) leaf blade divisions, 7) petiole pubescence and 8) below ground exterior color.)

In a further aspect, a carrot plant is provided, which statistically significantly differs from NUN 85931 in at least one morphological and/or physiological characteristics, but which does not differ significantly from NUN 85931 in the following distinguishing characteristics when grown under the same conditions (measured at market maturity/harvest stage): 1) average carrot length minus taproot, 2) average leaf petiole length from crown to first pinna, 3) average plant top height (from shoulder to top of crown), and 4) average plant top neck diameter; and which further does not significantly differ from the plant designated NUN 85931 in one, two, three or more of the following characteristics when grown under the same conditions (measured at market maturity): 5) number and prominence of secondary root scars, 6) leaf blade divisions, 7) petiole pubescence and 8) below ground exterior color.

In a further embodiment a carrot plant is provided, which (statistically significantly) differs from the carrot plant designated NUN 85931, representative seeds of said carrot plant having been deposited under accession number NCIMB 42390, in at least one, two, three, four, or five morphological and/or physiological characteristics when grown under the same environmental conditions, whereby the morphological and/or physiological characteristics are those of Table 1. The carrot plant does, thus, not differ in a statistically significant way from NUN 85931 in any of the morphological and/or physiological characteristics of Table 1 when grown under the same conditions, or only differs is one, two, three, four or five of the morphological and/or physiological characteristics of Table 1, while there is no significant difference in the other characteristics.

In one embodiment a carrot plant is provided, designated NUN 85931, which does not (statistically significantly) differ in any of the morphological and/or physiological characteristics of Table 1 from plants grown from seeds deposited under accession number NCIMB 42390 when grown under the same environmental conditions.

In yet another aspect of the invention, a tissue culture or cell-culture of regenerable cells of a carrot plant according to the invention is provided. The tissue culture or cell-culture will preferably be capable of regenerating carrot plants capable of expressing all of the physiological and morphological characteristics of the starting plant, and of regenerating plants having substantially the same genotype as the starting plant. Examples of some of the physiological and morphological characteristics of the hybrid NUN 85931 include those traits set forth in Table 1 herein when grown under the environmental conditions outlined herein with reference to the data of Table 1. The regenerable cells in such tissue or cell cultures may be derived, for example, from carrot explants, such as embryos, meristems, petioles, cuttings, protoplasts, cotyledons, pollen, leaves, nodes, anthers, roots, taproots, root tips, pistils, flowers, seed, stalks and stems. Still further, the present invention provides carrot plants regenerated from a tissue culture of the invention. These plants have all the physiological and morphological characteristics of a plant according to the invention.

In another aspect, the above described carrot plants are obtainable from in vitro cell or tissue cultures. As already elsewhere in this application, in vitro cell or tissue cultures are known in the art and can be used to either vegetatively reproduce the plant from which the cells or tissues were obtained or to identify and/or select a phenotypic variant (such as an EDV), and to regenerate such a variant. The phenotypic variant may, for example, be a somaclonal variant, mutant or off-type, but is preferably genetically stable. Thus, the variant phenotype is preferably genetically stable, also in the mature plants regenerated from the cell or tissue culture. That means, the phenotypic variant does not show variation in phenotype which are transient and are not genetically stable. Once selected, such selected variants can then in turn also be reproduced true to type using in vitro cell or tissue culture or by propagation via seed.

Thus in one aspect, a carrot plant is provided which is clonally propagated (it is a vegetative reproduction) from NUN 85931 cells or tissue and which comprises all the distinguishing characteristics of NUN 85931 when grown under the same environmental conditions. In another aspect it further comprises one or more of the further distinguishing characteristics. In yet another aspect it comprises all morphological and/or physiological characteristics of NUN 85931 as given in Table 1. And in yet a further aspect it comprises all morphological and/or physiological characteristics of NUN 85931 as given in Table 1, except that it significantly differs from NUN 85931 in one, two, three, four, or five of the morphological and/or physiological characteristics of Table 1.

The invention also concerns methods of vegetatively propagating a plant of the invention. In certain embodiments, the method comprises the steps of: (a) collecting tissue or cells capable of being propagated from a plant of the invention; (b) cultivating said tissue or cells to obtain proliferated shoots; and (c) rooting said proliferated shoots, to obtain rooted plantlets. Steps (b) and (c) may also be reversed, i.e. first cultivating said tissue to obtain roots and then cultivating the tissue to obtain shoots, thereby obtaining rooted plantlets. The rooted plantlets may then be further grown, to obtain plants. In one embodiment, the method further comprises step (d) growing plants from said rooted plantlets.

In still yet another aspect of the invention, processes are provided for producing carrot seeds, plants and roots, which processes generally comprise crossing a first parent carrot plant with a second parent carrot plant, wherein at least one of the first or second parent carrot plants is a plant according to the invention.

One embodiment of the invention refers to a method of producing a carrot plant comprising crossing a carrot plant of variety NUN 85931 with a second carrot plant one or more times such as one, two, three, four, five, six or more times. This method comprises in one embodiment selecting progeny from said crossing.

These processes may be further exemplified as processes for preparing hybrid carrot seed or plants, wherein a first carrot plant is crossed with a second carrot plant of a different, distinct genotype to provide a hybrid that has, as one of its parents, a plant of NUN 85931.

The present invention also provides the carrot seeds and plants produced by a process that comprises crossing a first parent carrot plant with a second parent carrot plant, wherein at least one of the first or second parent carrot plants is a plant provided herein, such as from variety NUN 85931. In another embodiment of the invention, carrot seed and plants produced by the process are first filial generation (F1) carrot seed and plants produced by crossing a plant in accordance with the invention with another, distinct plant. The present invention further contemplates plant parts of such an F1 hybrid carrot plant, and methods of use thereof. Therefore, certain exemplary embodiments of the invention provide an F1 hybrid carrot plant and seed thereof.

In another embodiment of the invention, carrot variety NUN 85931 is crossed to produce hybrid seed of the variety designated NUN 85931. In any cross herein, either parent may be the male or female parent. In these processes, crossing will result in the production of seed. The seed production occurs regardless of whether the seed is collected or not.

In certain embodiments, the invention provides methods of introducing a desired trait into a carrot plant comprising the steps of:
(a) crossing a plant of variety NUN 85931 with a second carrot plant that comprises a desired trait to produce F1 progeny,
(b) selecting an F1 progeny that comprises the desired trait(s), e.g., one, two, three or more desired trait(s),
(c) optionally selfing the F1 progeny one or more times to produce F2, F3, or further generation selfing progeny,
(d) crossing the selected F1 progeny or the selfing progeny with a plant of variety NUN 85931 to produce backcross progeny, and
(e) selecting backcross progeny comprising the desired trait(s) and which otherwise has all or essentially all the physiological and morphological characteristics of carrot variety NUN 85931,
(f) optionally, steps (d) and (e) can be repeated one or more times, e.g., three or more times such as three, four, five, six or seven times, in succession to produce higher backcross progeny (e.g. selected fourth, fifth, sixth, seventh or eighth or higher backcross progeny) that comprises the desired trait.

The invention also provides carrot plants produced by these methods; a representative sample of seed of NUN 85931 having been deposited under NCIMB Accession Number 42390.

In another aspect of the invention, a carrot plant of variety NUN 85931 comprising an added heritable trait is provided, e.g., an Essentially Derived Variety of NUN 85931 having one, two or three physiological and/or morphological characteristics which are different from those of NUN 85931 and which otherwise has all the physiological and morphological characteristics of NUN 85931, wherein a representative sample of seed of variety NUN 85931 has been deposited under NCIMB Accession Number 42390. The heritable trait may comprise a genetic locus that is, for example, a dominant or recessive allele (optionally including epigenetic modifications). In one embodiment of the invention, a plant of the invention is defined as comprising a single locus conversion. For example, one, two, three or more heritable traits may be introgressed at any particular locus using a different allele that confers the new trait or traits of interest. In specific embodiments of the invention, the single locus conversion confers one or more traits such as, for example, herbicide tolerance, insect resistance, disease resistance and modulation of plant metabolism and metabolite profiles. In further embodiments, the trait may be conferred by a naturally occurring gene introduced into the genome of the variety by backcrossing, a natural or induced mutation, a somaclonal variant, an off-type, or a transgene introduced through genetic transformation techniques into the plant or a progenitor of any previous generation thereof. When introduced through transformation, a genetic locus may comprise one or more genes integrated at a single chromosomal location. Thus, the invention comprises a method of producing a plant comprising an added desired trait, the method comprising introducing a transgene conferring a desired trait into a plant of carrot variety NUN 85931.

In still yet another aspect, the invention provides a method of determining the genotype of a plant of the invention comprising detecting in the genome of the plant at least a first polymorphism. The method may, in certain embodiments, comprise detecting a plurality of polymorphisms in the genome of the plant. For example, a sample of nucleic acid is obtained from a plant and a polymorphism or a plurality of polymorphisms is detected in said nucleic acids. The method may further comprise storing the results of the step of detecting the plurality of polymorphisms on a computer readable medium.

In one embodiment of the invention, the invention provides a method for producing a seed of a variety derived from NUN 85931 comprising the steps of (a) crossing a carrot plant of variety NUN 85931 with a second carrot plant; and (b) allowing seed of a variety NUN 85931-derived carrot plant to form. This method can further comprise steps of (c) crossing a plant grown from said variety NUN 85931-derived carrot seed with itself or a second carrot plant to yield additional variety NUN 85931-derived carrot seed; (d) growing said additional variety NUN 85931-derived carrot seed of step (c) to yield additional variety NUN 85931-derived carrot plants; and optionally (e) repeating the crossing and growing steps of (c) and (d) to generate further variety NUN 85931-derived carrot plants, e.g. one or more times such as two times, three times, three or more times such as four times, five times, six times, seven times or even more times. For example, the second carrot plant is of an inbred carrot variety, or alternatively, the second carrot plant in step c) is NUN 85931 or the male or female parent plant of NUN 85931.

In still yet another aspect, the present invention provides a method of producing a plant or a seed derived from variety NUN 85931, the method comprising the steps of: (a) preparing a progeny plant derived from said variety by crossing a plant of variety NUN 85931 with a second plant; and (b) allowing seed of a variety NUN 85931-derived carrot plant to form. In one embodiment, the second plant is a plant of an inbred line or of a wild accession of *Daucus carota*.

The method may additionally comprise: (c) crossing a plant grown from said variety NUN 85931-derived carrot seed with itself or a second carrot plant to yield additional variety NUN 85931-derived carrot seed; (d) growing said additional variety NUN 85931-derived carrot seed of step (c) to yield additional variety NUN 85931-derived carrot plants; and optionally (e) repeating the crossing and growing steps of (c) and (d) to generate further variety NUN 85931-derived carrot plants. For example, steps (c) and (d) may be repeated one or more times such as one, two, three, four, five or six, seven, eight, nine, ten, or more times to produce a further plant derived from the aforementioned starting variety. The further plant derived from variety NUN 85931 may be an inbred variety, and the aforementioned repeated crossing steps may be defined as comprising sufficient inbreeding to produce the inbred variety. In the method, it may be desirable to select particular plants resulting from step (c) for continued crossing according to steps (b) and (c). By selecting plants having one or more desirable traits, a plant is obtained which possesses some of the desirable traits of the starting plant as well as potentially other selected traits.

In certain embodiments, the present invention provides a method of producing a carrot root comprising: (a) obtaining a plant of the invention, wherein the plant has been cultivated to maturity, and (b) collecting a carrot from said plant.

The invention also provides for a food or feed product comprising or consisting of a plant part described herein preferably a carrot root or part thereof and/or an extract from a plant part described herein. The food or feed product may be fresh or processed, e.g., canned, dried, steamed, boiled, fried, blanched and/or frozen, comprise extracted juices, etc. Genetic material of the plant of the invention may still be obtained from the food or feed product.

In still another embodiment the invention relates to a seed or plant produced by selfing a plant of the invention.

In another aspect the invention refers to packages, e.g., a container, a bag and the like, comprising at least one of the following: seeds or seed pellets of carrot variety designated NUN 85931, carrot plant(s) designated NUN 85931, parts thereof (e.g. roots), progeny of a carrot plant designated NUN 85931, parts thereof, EDV of a plant designated NUN 85931 or parts thereof.

In one embodiment any of the plant of the invention comprises at least 3, 4, 5 or more of the following (average) morphological and/or physiological characteristics (i.e distinguishing characteristics) (measured at market maturity/harvest stage): 1) a carrot length (minus taproot) between about 28 and 40 cm, or preferably between about 31 and 37 cm or between about 33 and 35 cm or even between about 33.5 and about 34.5 cm; 2) a leaf petiole length from crown to first pinna that is between about 20 and 30 cm, or preferably between about 23 and 26 cm or between about 24.0 and 26.0 cm or even between about 24.5 and about 25.5 cm; 3) a plant top height (from shoulder to top of crown) between about 32 and 52 cm, or preferably between about 37 and 47 cm or between about 40 and 44 cm or even between about 41.8 and about 42.8 cm, 4) an average plant top neck diameter of between about 9.0 and 12.0 mm, or preferably between about 9.5 and 11.5 mm, or between about 10.0 and 11.0 mm, or even between about 10.3 and about 10.7 mm; 5) a carrot surface that has no secondary root scars, which thus are not prominent; 6) medium leaf blade divisions; 7) leaf petiole pubescence that is present; 8) a below ground exterior color that is orange, e.g. RHS colour chart 170A.

Another aspect refers to a carrot plant, or a part thereof, having all or essentially all the physiological and morphological characteristics of a carrot plant of carrot variety NUN 85931 when grown under the same conditions.

The root of carrot variety NUN 85931 has an orange color.

Also provided are one or more progeny plants (offspring or descendants) of a carrot plant designated NUN 85931 obtained by further breeding with said variety designated NUN 85931. Said progeny plant(s) has/have essentially all physiological and morphological characteristics of variety NUN 85931 when grown under the same environmental conditions. In one embodiment, said progeny plant(s) has/have 3, 4, 5, 6, 7, 8, or more, or all of, the following (average) characteristics measured at market maturity (see USDA descriptors):

- a cut and peel type;
- a semi-erect habit;
- a single top attachment;
- a leaf blade color that is medium green;
- a leaf petiole length of about 25.0 cm; e.g. between about 20 and 30 cm, or preferably between about 23 and 27 cm or between about 24.0 and 26.0 cm or even between about 24.5 and about 25.5 cm;
- no leaf petiole anthocyanin;
- a root core (phloem) thickness of about 6.6 mm, e.g. between about 4 and 10 mm, or preferably between 5 and 8 mm, or even between about 6 and 7 mm;
- a root core (xylem) thickness of about 6.4 mm, e.g. between about 4 and 10 mm, or preferably between 5 and 8 mm, or even between about 6 and 7 mm;
- a taproot length of about 53.6 mm, e.g. between about 44 and 64 mm, or between about 48 and 60 mm, or even between about 52 and 56 mm;
- a carrot shoulder diameter of about 24.3 mm; e.g. between about 17 and 33 mm, or preferably between about 20 and 28 mm, or even between about 23 and about 25 mm;
- a carrot midpoint diameter of about 19.7 mm; e.g. between about 14 and 28 mm, or preferably between about 16 and 24 mm, or even between about 19 and about 21 mm;
- No exposure above ground;
- a conic root shape with a level root collar;
- a a rounded root shoulder with a pointed base;
- a very smooth surface;
- no halo and faint root zoning;
- a flavor that is mildly harsh and moderately sweet;
- orange below ground exterior color of shoulder and skin (e.g. RHS chart: greyed orange 170A);
- orange interior phloem color (e.g. RHS chart: orange 28B)
- male sterile flowers with petaloid anthers.

Any embodiment discussed herein with respect to one aspect of the invention applies to other aspects of the invention as well, unless specifically noted.

GENERAL DEFINITIONS

In the description and tables herein, a number of terms are used. In order to provide a clear and consistent understanding of the specification and claims, the following definitions are provided:

The term "about" is used to indicate that a value includes the standard deviation of error for the device or method being employed to determine the value.

The use of the term "or" in the claims is used to mean "and/or" unless explicitly indicated to refer to alternatives only or the alternatives are mutually exclusive, although the disclosure supports a definition that refers to only alternatives and to "and/or."

When used in conjunction with the word "comprising" or other open language in the claims, the words "a" and "an" denote "one or more" unless specifically noted.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and also covers other unlisted steps. Similarly, any plant that "comprises," "has" or "includes" one or more traits is not limited to possessing only those one or more traits and covers other unlisted traits. The terms mentioned above also comprise the term "contain" which is limited to specific embodiments. Thus, one embodiment of the invention, when the terms "comprise," "have" and "include" are used to describe a plant, part thereof or a process, refers to an embodiment wherein the limiting term "contain" is used.

"Carrot" refers herein to a plant of the species *Daucus carota* and parts thereof, e.g., the (edible) root. The most commonly eaten part of a carrot is a root, although the greens are edible as well. A carrot is a root vegetable plant, the root (carrot root) is usually orange in color, though purple, red, white, cream, and yellow varieties exist as well. At the tip of a carrot root is a thin taproot while at the other end (base) of a carrot root the green is attached.

"Cultivated carrot" refers to plants of *Daucus carota*, i.e. varieties, breeding lines or cultivars of the species *Daucus carota*, cultivated by humans and having good agronomic characteristics; preferably such plants are not "wild plants", i.e. plants which generally have much poorer yields and poorer agronomic characteristics than cultivated plants and e.g. grow naturally in wild populations. "Wild plants" include for example ecotypes, PI (Plant Introduction) lines, landraces or wild accessions or wild relatives of a species.

"USDA descriptors" are the plant variety descriptors described for carrot in the "Objective description of Variety Carrot *Daucus carota*)", ST-470-78 (as published by U.S. Department of Agriculture, Agricultural Marketing Service, Science and Technology, Plant Variety Protection Office, Beltsville, Md. 20705 (available on the world wide web at ams.usda.gov/AMSv1.0/) and which can be downloaded from the world wide web at ams.usda.gov/AMSv1.0/getfile?dDocName=STELDEV3002673.

"UPOV descriptors" are the plant variety descriptors described for carrot in the "Guidelines for the Conduct of Tests for Distinctness, Uniformity and Stability, TG/49/8 (Geneva 2007), as published by UPOV (International Union for the Protection of New Varieties and Plants, available on the world wide web at upov.int) and which can be downloaded from the world wide web at upov.int/edocs/tgdocs/en/tg049.pdf and is herein incorporated by reference in its entirety.

"RHS" refers to the Royal Horticultural Society of England which publishes an official botanical color chart quantitatively identifying colors according to a defined numbering system, The chart may be purchased from Royal Horticulture Society Enterprise Ltd RHS Garden; Wisley, Woking; Surrey GU236QB, UK, e.g., the RHS color chart: 2007 (The Royal Horticultural Society, charity No: 222879, PO Box 313 London SW1P2PE; sold by, e.g., TORSO-VERLAG, Obere Grüben 8•D-97877 Wertheim, Article-No.: Art62-00008 EAN-Nr.: 4250193402112).

"Core" refers to the phloem and xylem of the root, i.e the central vascular tissue. "Cortex" refers to the non-vascular tissue surrounding the core tissue.

"Genotype" refers to the genetic composition of a cell or organism.

"Phenotype" refers to the detectable characteristics of a cell or organism, which characteristics are the manifestation of gene expression.

As used herein, the term "plant" includes the whole plant or any parts or derivatives thereof, preferably having the same genetic makeup as the plant from which it is obtained, such as plant organs (e.g. harvested or non-harvested carrot root), plant cells, plant protoplasts, plant cell and/or tissue cultures from which whole plants can be regenerated, plant calli, plant cell clumps, plant transplants, seedlings, hypocotyl, cotyledon, plant cells that are intact in plants, plant clones or micropropagations, or parts of plants (e.g. harvested tissues or organs), such as plant cuttings, vegetative propagations, embryos, pollen, ovules, flowers, leaves, seeds, clonally propagated plants, roots, taproots, stems, root tips, grafts, parts of any of these and the like. Also any developmental stage is included, such as seedlings, cuttings prior or after rooting, mature plants, roots or leaves. Alternatively, plant parts may also include a plant seed which comprises one or two sets of chromosomes derived from the parent plant.

"Harvested plant material" refers herein to plant parts (e.g. a root detached from the whole plant) which have been collected for further storage and/or further use.

"Harvested seeds" refers to seeds harvested from a line or variety, e.g. produced after self-fertilization or cross-fertilization and collected.

A plant having "(essentially) all the physiological and morphological characteristics" means a plant having essentially all or all the physiological and morphological characteristics when grown under the same environmental conditions of the plant of NUN 85931 from which it was derived, e.g. the progenitor plant, the parent, the recurrent parent, the plant used for tissue- or cell culture, etc. The skilled person will understand that a comparison between carrot varieties should occur when said varieties are grown under the same environmental conditions. For example, the plant may have all characteristics mentioned in Table 1 when grown under the environmental conditions outlined herein with reference to the data of Table 1. In certain embodiments, the plant having "essentially all the physiological and morphological characteristics" are plants having all the physiological and morphological characteristics of Table 1, except for certain characteristics (such as one, two or three) mentioned, e.g. the characteristic(s) derived from a converted or introduced gene or trait and/or except for the characteristics which differ in an EDV. So, the plant may have all characteristics mentioned in Table 1, except for one, two or three characteristics of Table 1, in which the plant may thus differ.

A plant having one or more or all "essential physiological and/or morphological characteristics" or one or more "distinguishing characteristics" (such as one, two, three, four or five) refers to a plant having (or retaining) one or more, or all, or retaining all except one, two or three of the distinguishing characteristics mentioned in Table 1 when grown under the same environmental conditions that distinguish NUN 85931 from the most similar variety PS 1441. For example, such distinguishing characteristics (measured at market maturity/harvest stage) being selected from (but not limited to): 1) average carrot length (minus taproot), 2) average leaf petiole length from crown to first pinna, 3) average plant top height (from shoulder to top of crown), 4) average plant top neck diameter, 5) number and prominence of secondary root scars, 6) leaf blade divisions, 7) petiole pubescence and 8) below ground exterior color. The physiological and/or morphological characteristics mentioned above are commonly evaluated at significance levels of 1%, 5%, 8% or 10% significance level, when measured under the same environmental conditions. For example, a progeny plant of NUN 85931 may have one or more (or all, or all except one, two or three) of the essential physiological and/or morphological characteristics of NUN 85931 listed in Table 1, or one or more or all (or all except one, two or three) of the distinguishing characteristics of NUN 85931 listed in Table 1 and above, as determined at the 1% or 5% significance level when grown under the same environmental conditions.

Physiological and/or morphological characteristics which are "substantially equivalent" or "not significantly different" or "not significantly differ" refers to a characteristic that, when compared, does not show a statistically significant difference (e.g., $p>0.05$ using ANOVA (analysis of variance)) from the mean. Vice versa, "significantly different" or "statistically significantly different" refers to a characteristic that, when compared, does show a statistically significant difference (e.g., $p<0.05$ using ANOVA) from the mean.

As used herein, the term "variety" or "cultivar" means a plant grouping within a single botanical taxon of the lowest known rank, which grouping, irrespective of whether the conditions for the grant of a breeder's right are fully met, can be defined by the expression of the characteristics resulting from a given genotype or combination of genotypes, distinguished from any other plant grouping by the expression of at least one of the said characteristics and considered as a unit with regard to its suitability for being propagated unchanged.

The terms "gene converted" or "conversion plant" in this context refer to carrot plants which are often developed by backcrossing wherein essentially all of the desired morphological and/or physiological characteristics of parent are recovered in addition to the one or more genes transferred into the parent via the backcrossing technique or via genetic engineering. Likewise a "Single Locus Converted (Conversion) Plant" refers to plants which are often developed by plant breeding techniques comprising or consisting of backcrossing, wherein essentially all of the desired morphological and physiological characteristics of a carrot variety are recovered in addition to the characteristics of the single locus having been transferred into the variety via, e.g., the backcrossing technique and/or by genetic transformation. Likewise, a double loci converted plant/a triple loci converted plant refers to plants having essentially all of the desired morphological and/or physiological characteristics of given variety, expect that at two or three loci, respectively, it contains the genetic material (e.g., an allele) from a different variety.

A variety is referred to as an "Essentially Derived Variety" (EDV) i.e., shall be deemed to be essentially derived from another variety, "the initial variety" when (i) it is predominantly derived from the initial variety, or from a variety that is itself predominantly derived from the initial variety, while retaining the expression of the essential characteristics that result from the genotype or combination of genotypes of the initial variety; (ii) it is clearly distinguishable from the initial variety; and (iii) except for the differences which result from the act of derivation, it conforms to the initial variety in the expression of the essential characteristics that result from the genotype or combination of genotypes of the initial variety. Thus, an EDV may be obtained for example by the selection of a natural or induced mutant, or of a somaclonal variant, or an off-type, or the selection of a variant individual from plants of the initial variety, backcrossing, or transformation by genetic engineering. Such a variant may be selected at any time, e.g. in the field or greenhouse, during breeding, during or after in vitro culture of cells or tissues, during regeneration of plants, etc. The term EDV, thus, also encompassed a "phenotypic variant" derived from NUN 85931 seed, plant tissue or cells. In one embodiment, an EDV is a gene converted plant.

"Plant line" is for example a breeding line which can be used to develop one or more varieties.

"Hybrid variety" or "F1 hybrid" refers to the seeds of the first generation progeny of the cross of two non-isogenic plants. For example, the female parent is pollinated with pollen of the male parent to produce hybrid (F1) seeds on the female parent.

"Progeny" as used herein refers to plants derived from a plant designated NUN 85931. Progeny may be derived by regeneration of cell culture or tissue culture or parts of a plant designated NUN 85931 or selfing of a plant designated NUN 85931 or by producing seeds of a plant designated NUN 85931. In further embodiments, progeny may also encompass plants derived from crossing of at least one plant designated NUN 85931 with another carrot plant of the same or another variety or (breeding) line, or with a wild carrot plant, backcrossing, inserting of a locus into a plant or selecting a plant comprising a mutation or selecting a variant. A progeny is, e.g., a first generation progeny, i.e. the progeny is directly derived from, obtained from, obtainable from or derivable from the parent plant by, e.g., traditional breeding methods (selfing and/or crossing) or regeneration. However, the term "progeny" generally encompasses further generations such as second, third, fourth, fifth, sixth, seventh or more generations, i.e., generations of plants which are derived from, obtained from, obtainable from or derivable from the former generation by, e.g., traditional breeding methods, regeneration or genetic transformation techniques. For example, a second generation progeny can be produced from a first generation progeny by any of the methods mentioned above. Especially progeny of NUN 85931 which are EDVs or which retain all (or all except 1, 2 or 3) physiological and/or morphological characteristics of NUN 85931 listed in Table 1, or which retain all (or all except 1, 2, or 3) of the distinguishing characteristics of NUN 85931 described elsewhere herein and in Table 1, are encompassed herein.

The term "traditional breeding techniques" encompasses herein crossing, selfing, selection, double haploid production, embryo rescue, protoplast fusion, marker assisted selection, mutation breeding etc. as known to the breeder (i.e. methods other than genetic modification/transformation/transgenic methods), by which, for example, a genetically heritable trait can be transferred from one carrot line or variety to another.

"Crossing" refers to the mating of two parent plants.

"Cross-pollination" refers to the fertilization by the union of two gametes from different plants.

"Backcrossing" is a traditional breeding technique used to introduce a trait into a plant line or variety. The plant containing the trait is called the donor plant and the plant into which the trait is transferred is called the recurrent parent. An initial cross is made between the donor parent and the recurrent parent to produce progeny plants. Progeny plants which have the trait are then crossed to the recurrent parent. After several generations of backcrossing and/or selfing the recurrent parent comprises the trait of the donor. The plant generated in this way may be referred to as a "single trait converted plant".

"Selfing" refers to self-pollination of a plant, i.e., the transfer of pollen from the anther to the stigma of the same plant.

"Regeneration" refers to the development of a plant from cell culture or tissue culture or vegetative propagation.

"Vegetative propagation", "vegetative reproduction" or "clonal propagation" are used interchangeably herein and mean the method of taking part of a plant and allowing that plant part to form at least roots where plant part is, e.g., defined as or derived from (e.g. by cutting of) leaf, pollen, embryo, cotyledon, hypocotyl, cells, nodes, protoplasts, meristematic cell, root, root tip, pistil, anther, flower, shoot tip, shoot, stem, petiole, etc. When a whole plant is regenerated by vegetative propagation, it is also referred to as a vegetative propagation.

The term "locus" (plural loci) means a specific place or places or a site of a DNA sequence on a chromosome where for example a gene or genetic marker is found. A locus may confer a specific trait.

"Linkage" or "genetic linkage" is the tendency of genes or molecular markers that are located proximal to each other on a chromosome to be inherited together during meiosis. Genes or molecular markers whose loci are nearer to each other are less likely to be separated onto different chromatids during chromosomal crossover, and are therefore said to be genetically linked.

"Marker" or "molecular marker" refers to a readily detectable DNA sequence or nucleotide, which may be genetically closely linked to a gene or locus. Such closely linked markers can be used in MAS (marker assisted selection) of the gene or locus.

"Marker assisted selection" or "MAS" is a process of using the presence of molecular markers, which are genetically linked to a particular locus or to a particular chromosome region, to select plants for the presence of the specific locus or region.

The term "allele(s)" means any of one or more alternative forms of a gene at a particular locus, all of which alleles relate to one trait or characteristic at a specific locus. In a diploid cell of an organism, alleles of a given gene are located at a specific location, or locus (loci plural) on a chromosome. One allele is present on each chromosome of the pair of homologous chromosomes. A diploid plant species may comprise a large number of different alleles at a particular locus. These may be identical alleles of the gene (homozygous) or two different alleles (heterozygous).

As used herein, the terms "resistance" and "tolerance" are used interchangeably to describe plants that show no symptoms or significantly reduced symptoms to a specified biotic pest, pathogen, abiotic influence or environmental condition. These terms are also used to describe plants showing some symptoms but that are still able to produce marketable product with an acceptable yield.

"Tissue Culture" refers to a composition comprising isolated cells or tissues of the same or a different type or a collection of such cells organized into parts of a plant.

"Transgene" or "chimeric gene" refers to a genetic locus comprising a DNA sequence which has been introduced into the genome of a carrot plant by transformation. A plant comprising a transgene stably integrated into its genome is referred to as "transgenic plant".

"Haploid" refers to a cell or organism having one set of the two sets of chromosomes in a diploid.

"Diploid" refers to a cell or organism having two sets of chromosomes.

"Polyploid" refers to a cell or organism having three or more complete sets of chromosomes.

"Average" refers herein to the arithmetic mean.

The term "mean" refers to the arithmetic mean of several measurements. The skilled person understands that the appearance of a plant depends to some extent on the growing conditions of said plant. Thus, the skilled person will know typical growing conditions for carrot described herein. The mean, if not indicated otherwise within this application, refers to the arithmetic mean of measurements on at least 10 different, randomly selected plants or plant parts of a variety or line.

Seeds

Also provided are seeds of carrot variety NUN 85931, i.e. seeds from which the variety can be grown.

In one embodiment, a plurality of NUN 85931 seeds are packaged into small and/or large containers (e.g., bags, cartons, cans, etc.). Seeds may be treated with one or more chemical compounds and/or biological control and/or crop protection agents (e.g. to improved germination, insecticidal-, acaricidal-, nematicidal-, moluscicidal- or fungicidal- compounds or compositions, etc.) and/or seeds may be primed. Biological control agents are one or more microorganisms which protect the seed or seedling against pathogens. For example, strains of bacteria and/or fungi, such as bacteria of the species of *Streptomyces, Pseudomonas, Bacillus* and *Enterobacter* or fungi of the species *Phomopsis, Ectomycorrhizae, Trichoderma, Cladosporium* and *Gliocladium*. In another embodiment, seeds may additionally be (film-) coated or pelleted.

Priming is a water-based process that is performed on seeds to increase uniformity of germination and emergence from the soil, and thus enhance vegetable stand establishment. Methods how to prime carrot seeds are well known in the art, see WO2008/107097, describing different priming methods, such as hydro-priming (including drum-priming), osmopriming and solid-matrix priming, which can be used. The priming process may also be combined with the chemical compounds or compositions and/or biological control agent treatment, so seeds may e.g. be hydrated in a first step, dried in a second step and treated in a third step with one or more seed treatment compounds or compositions. Priming is also sometimes referred to as seed conditioning.

Hydropriming includes those techniques in which seeds are allowed to take up water for a short period or at low temperatures, mostly at ample water supply. These techniques are sometimes also referred to as soaking or steeping. With osmopriming, the seeds are exposed to an osmotic solution (see e.g. WO2008/107097).

With solid matrix priming (SMP), seeds are mixed with water and solid carriers. Examples of solid carriers are vermiculite and diatomaceous silica products. The water is taken up by the seeds as well as absorbed on the solid particle surfaces, which in this way control the water uptake of the seeds. In addition to using particle-like carriers, SMP can be carried out using, amongst others, moist towels, gunny bags, moist sand, sterilised compost or press mud as well.

(Film-)coating is a method for seed enhancement well known in the art. Seed is enveloped, aiming at one or more of the following effects: improving the germination characteristics, providing various additives, protecting the seeds, preventing dust formation, improve cosmetic appearance and/or field visibility or adjusting the seed shape or size to improve mechanical or automated handling. The seed is (film-)coated with a composition generally comprising a binder, a pigment or dye and optionally one or more active ingredients. (Film-) coating procedures available to persons skilled in the art include drum coaters, fluidized bed techniques, rotary coaters, spouted beds and film-forming compositions. (Film-) coats can be applied directly on seed or as an additional layer on seed that already has an envelope.

Pelleting is another method for seed enhancement well known in the art. Clay and/or other materials, optionally mixed with a binder and/or other additives are applied to the seed, enveloping it and providing improved uniformity shape and size as well as increasing weight or density for automated handling. Additional effects may include: improving germination characteristics, providing various additives, protecting seeds, improving cosmetic appearance and/or field visibility. Procedures for pelleting seeds known to persons skilled in the art include the use drum pelleters, rotating pelleting machines and seed coating systems.

So, in one aspect seeds of NUN 85931 are provided wherein said seeds are primed seeds and/or (film-)coated seeds and/or pelleted seeds and/or chemically and/or biologically treated seeds, comprising one or more chemical compounds or compositions and/or one or more biological control agents, selected from the group consisting of: a compound that improves germination, an insecticidal compound, a moluscicidal compound, an acaricidal compound, a nematicidal compound, and a fungicidal compound.

Breeding with Carrot Plants of the Invention

One aspect of the current invention concerns methods for crossing a carrot variety provided herein with itself or a second carrot plant and the seeds and plants produced by such methods. These methods can be used for propagation of a variety provided herein, or can be used to produce hybrid carrot seeds and the plants grown therefrom. Such hybrid seeds can be produced by crossing two parent lines or varieties to produce the hybrid variety.

In one embodiment of the invention, the first step in "crossing" comprises planting seeds of a first and a second parent carrot plant, often in proximity so that pollination will occur for example, mediated by insect vectors. Alternatively, pollen can be transferred manually. Where the plant is self-pollinated, pollination may occur without the need for direct human intervention other than plant cultivation.

A second step may comprise cultivating or growing the seeds of the first and the second parent carrot plants into plants that bear flowers. A third step may comprise preventing self-pollination of the plants. Self-incompatibility systems or male sterility (nuclear or cytoplasmic male sterility) may be used in some hybrid crops for the same purpose. In the production of hybrid carrot varieties, cytoplasmic male sterility (CMS) is widely used (see Simon et al. 2008, infra). The CMS parent line is cross pollinated with the pollen of the male-fertile parent line. The F1 seeds, i.e. the seeds from which the hybrid carrot variety is grown, are harvested from the CMS parent line. They may then be dried and cleaned, primed, pelleted, (film-)coated and/or treated with chemical compounds (e.g. fungicides, moluscicides, acaricides, nematicides, insecticides, etc.), before being packaged for sale.

A fourth step for a hybrid cross may comprise cross-pollination between the first and second parent carrot plants. In certain embodiments, pollen may be transferred manually or by the use of insect vectors. Yet another step comprises harvesting the seeds from at least one of the parent carrot plants. The harvested seed can be grown to produce a carrot plant or hybrid carrot plant.

The development of new varieties using one or more starting varieties is well known in the art. In accordance with the invention, a new hybrid cross in carrots is developed by using cytoplasmic male sterility (CMS) (see, e.g. pages 337-338 in Simon et al. 2008, Chapter "Carrot" pp 327-357; in the book "Vegetables II Volume 2, 2008; ISBN 978-O-387-74108-6).

Also in accordance with the invention, novel varieties may be created by crossing a plant of the invention followed by multiple generations of breeding according to such well known methods. New varieties may be created by crossing with any second plant. In selecting such a second plant to cross for the purpose of developing novel varieties, it may be desired to choose those plants that either themselves exhibit one or more selected desirable characteristics or that exhibit the desired characteristic(s) when in hybrid combination. Once initial crosses have been made, inbreeding and selection take place to produce new varieties. For development of a uniform variety, often five or more generations of selfing and selection are involved.

Uniform varieties of new varieties may also be developed by way of double-haploids. This technique allows the creation of true breeding varieties without the need for multiple generations of selfing and selection. In this manner, true breeding varieties can be produced in as little as one generation. Haploid cells, such as microspores, pollen, anther cultures, or ovary cultures can be used. The chromosomes of the haploid cells may then be doubled autonomously, or by chemical treatments (e.g. colchicine treatment). From the double-haploid cells, fertile homozygous plants are obtained. In accordance with the invention, any of such techniques may be used in connection with a plant of the invention and progeny thereof to achieve a homozygous variety.

Backcrossing can also be used to improve an inbred plant. Backcrossing transfers one or more heritable traits from one inbred or non-inbred source to an inbred that lacks those traits. The exact backcrossing protocol will depend on the characteristic(s) or trait(s) being altered to determine an appropriate testing protocol. When the term variety NUN 85931 is used in the context of the present invention, this also includes plants modified to include at least a first desired heritable trait such as one, two or three desired heritable trait(s).

This can be accomplished, for example, by first crossing a superior inbred (recurrent parent) to a donor inbred (non-recurrent parent), which carries the appropriate genetic information (e.g., an allele) at the locus or loci relevant to the trait in question. The progeny of this cross are then mated back to the recurrent parent followed by selection in the resultant progeny (first backcross generation, or BC1) for the desired trait to be transferred from the non-recurrent parent. After five or more backcross generations with selection for the desired trait, the progeny are heterozygous at loci controlling the characteristic being transferred, but are like the superior parent for most or almost all other loci. The last backcross generation would be selfed to give pure breeding progeny for the trait being transferred.

The parental carrot plant which contributes the desired characteristic or characteristics is termed the non-recurrent parent because it can be used one time in the backcross protocol and therefore need not recur. The parental carrot plant to which the locus or loci from the non-recurrent parent are transferred is known as the recurrent parent as it is used for several rounds in the backcrossing protocol.

Many single locus traits have been identified that are not regularly selected for in the development of a new inbred but that can be improved by backcrossing techniques. Single locus traits may or may not be transgenic; examples of these traits include, but are not limited to, male sterility, herbicide resistance, resistance to bacterial, fungal, or viral disease, insect resistance, restoration of male fertility, modified fatty acid or carbohydrate metabolism and enhanced nutritional quality. These comprise genes generally inherited through the nucleus.

Direct selection or screening may be applied where the single locus (e.g. allele) acts in a dominant fashion. For example, when selecting for a dominant allele providing resistance to a bacterial disease, the progeny of the initial cross can be inoculated with bacteria prior to the backcrossing. The inoculation then eliminates those plants which do not have the resistance, and only those plants which have the resistance allele are used in the subsequent backcross. This process is then repeated for all additional backcross generations.

Although backcrossing methods are simplified when the characteristic being transferred is a dominant allele, recessive, co-dominant and quantitative alleles may also be transferred. In this instance, it may be necessary to introduce a test of the progeny to determine if the desired locus has been successfully transferred. In the case where the non-recurrent variety was not homozygous, the F1 progeny would not be equivalent. F1 plants having the desired genotype at the locus of interest could be phenotypically selected if the corresponding trait was phenotypically detectable in a heterozygous or hemizygous state. In the case where a recessive allele is to be transferred and the corresponding trait is not phenotypically detectable in the heterozygous of hemizygous state, the resultant progeny can be selfed, or crossed back to the donor to create a segregating population for selection purposes. Non-phenotypic tests may also be employed. Selected progeny from the segregating population can then be crossed to the recurrent parent to make the first backcross generation (BC1).

Molecular markers may also be used to aid in the identification of the plants containing both a desired trait and having recovered a high percentage of the recurrent parent's genetic complement. Selection of carrot plants for breeding is not necessarily dependent on the phenotype of a plant and instead can be based on genetic investigations. For example, one can utilize a suitable genetic marker which is closely genetically linked to a trait of interest. One of these markers can be used to identify the presence or absence of a trait in the offspring of a particular cross, and can be used in selection of progeny for continued breeding. This technique is commonly referred to as marker assisted selection. Any other type of genetic marker or other assay that is able to identify the relative presence or absence of a trait of interest in a plant can also be useful for breeding purposes. Procedures for marker assisted selection applicable to the breeding of carrot are well known in the art. Such methods will be of particular utility in the case of recessive traits and variable phenotypes, or where conventional assays may be more expensive, time consuming or otherwise disadvantageous. Types of genetic markers which could be used in accordance with the invention include, but are not necessarily limited to, Simple Sequence Length Polymorphisms (SSLPs), Simple Sequence Repeats (SSR), Randomly Amplified Polymorphic DNAs (RAPDs), DNA Amplification Fingerprinting (DAF), Sequence Characterized Amplified Regions (SCARs), Arbitrary Primed Polymerase Chain Reaction (AP-PCR), Amplified Fragment Length Polymorphisms (AFLPs), and Single Nucleotide Polymorphisms (SNPs).

Carrot varieties can also be developed from more than two parents. The technique, known as modified backcrossing, uses different recurrent parents during the backcrossing. Modified backcrossing may be used to replace the original recurrent parent with a variety having certain more desirable characteristics or multiple parents may be used to obtain different desirable characteristics from each.

The variety of the present invention is particularly well suited for the development of new varieties based on the elite nature of the genetic background of the variety. In selecting a second plant to cross with NUN 85931 for the purpose of developing novel carrot varieties, it will typically be preferred to choose those plants that either themselves exhibit one or more selected desirable characteristics or that exhibit the desired characteristic(s) when in hybrid combination. Examples of desirable characteristics may include, but are not limited to herbicide tolerance, pathogen resistance (e.g., insect resistance, nematode resistance, resistance to bacterial, fungal, and viral disease), cytoplasmic male sterility (CMS), improved harvest characteristics, enhanced nutritional quality, increased antioxidant content, improved processing characteristics, high yield, improved characteristics related to the carrot root flavor, texture, size, shape, durability, shelf life, and yield, increased soluble solids content, uniform ripening, delayed or early ripening, seedling vigor, adaptability for soil conditions, and adaptability for climate conditions.

Plants of the Invention Derived by Genetic Engineering

Many useful traits that can be introduced by backcrossing, as well as directly into a plant, are those that are introduced by genetic transformation techniques. Genetic transformation may therefore be used to insert a selected transgene into the carrot variety of the invention or may, alternatively, be used for the preparation of varieties containing transgenes that can be subsequently transferred to the variety of interest by crossing. Methods for the transformation of plants, including carrot, are well known to those of skill in the art. Techniques which may be employed for the genetic transformation of carrot include, but are not limited to *Agrobacterium*-mediated transformation, microprojectile bombardment, direct DNA uptake by protoplasts and electroporation.

The most common system utilizes *Agrobacterium*-mediated transfer for introducing gene loci into plant cells of *Daucus carota* (see, e.g., Rafal Baranski, 2008). An advantage of the technique is that DNA can be introduced into whole plant tissues, thereby bypassing the need for regeneration of an intact plant from a protoplast. Modern *Agrobacterium* transformation vectors are capable of replication in *E. coli* as well as *Agrobacterium*, allowing for convenient manipulations. Moreover, recent technological advances in vectors for *Agrobacterium*-mediated gene transfer have improved the arrangement of genes and restriction sites in the vectors to facilitate the construction of vectors capable of expressing various polypeptide coding genes. The vectors described have convenient multi-linker regions flanked by a promoter and a polyadenylation site for direct expression of inserted polypeptide coding genes. Additionally, *Agrobacterium* containing both armed and disarmed Ti genes can be used for transformation.

Exemplary nucleic acids which may be introduced to the carrot varieties of this invention include, for example, DNA sequences or genes from another species, or even genes or sequences which originate with or are present in the same species, but are incorporated into recipient cells by genetic engineering methods rather than classical reproduction or breeding techniques. However, the term "exogenous" is also intended to refer to genes that are not normally present in the cell being transformed, or perhaps simply not present in the form, structure, etc., as found in the transforming DNA segment or gene, or genes which are normally present and that one desires to express in a manner that differs from the natural expression pattern, e.g., to over-express. Thus, the term "exogenous" gene or DNA is intended to refer to any gene or DNA segment that is introduced into a recipient cell, regardless of whether a similar gene may already be present in such a cell. The type of DNA included in the exogenous DNA can include DNA which is already present in the plant cell, DNA from another plant, DNA from a different organism, or a DNA generated externally, such as a DNA sequence containing an antisense message of a gene, or a DNA sequence encoding a synthetic or modified version of a gene.

Many hundreds if not thousands of different genes are known and could potentially be introduced into a carrot plant according to the invention. Non-limiting examples of particular genes and corresponding phenotypes one may choose to introduce into a carrot plant include one or more genes for insect tolerance, such as a *Bacillus thuringiensis* (B.t.) gene, fungal disease tolerance, herbicide tolerance such as genes conferring glyphosate tolerance or glufosinate tolerance, and genes for quality improvements such as yield, nutritional enhancements, environmental or stress tolerances, or any desirable changes in plant physiology, growth, development, morphology or plant product(s).

Still yet another aspect of the invention refers to the genetic complement of a carrot plant variety of the invention. The phrase "genetic complement" is used to refer to the aggregate of nucleotide sequences, the expression of which defines the phenotype of, in the present case, a carrot plant of, or a cell or tissue of that plant. A genetic complement thus represents the genetic makeup of a cell, tissue or plant, and a hybrid genetic complement represents the genetic make-up of a hybrid cell, tissue or plant. The invention thus provides carrot plant cells that have a genetic complement in accordance with the carrot plant cells disclosed herein, and plants, seeds and plants containing such cells.

Plant genetic complements may be assessed by genetic marker profiles, and by the expression of phenotypic traits that are characteristic of the expression of the genetic complement, e.g., gene expression profiles, gene product expression profiles and isozyme typing profiles. It is understood that a plant of the invention or a first generation progeny thereof could be identified by any of the many well-known techniques such as, for example, Simple Sequence Length Polymorphisms (SSLPs), Randomly Amplified Polymorphic DNAs (RAPDs), DNA Amplification Fingerprinting (DAF), Sequence Characterized Amplified Regions (SCARs), Arbitrary Primed Polymerase Chain Reaction (AP-PCR), Amplified Fragment Length Polymorphisms (AFLPs) (see, e.g., EP 534 858), and Single Nucleotide Polymorphisms (SNPs).

In still yet another aspect, the present invention provides hybrid genetic complements, as represented by carrot plant cells, tissues, plants, and seeds, formed by the combination of a haploid genetic complement of a carrot plant of the invention with a haploid genetic complement of a second carrot plant, preferably, another, distinct carrot plant. In another aspect, the present invention provides a carrot plant regenerated from a tissue culture that comprises a hybrid genetic complement of this invention.

Alternatively, the DNA coding sequences can affect these phenotypes by encoding a non-translatable RNA molecule that causes the targeted inhibition of expression of an endogenous gene, for example via antisense- or cosuppression-mediated mechanisms. The RNA could also be a catalytic RNA molecule (e.g., a ribozyme) engineered to cleave a desired endogenous mRNA product. Thus, any gene which produces a protein or mRNA which expresses a phenotype or morphology change of interest is useful for the practice of the present invention.

Deposit Information

A total of 2500 seeds of the variety NUN 85931 were deposited according to the Budapest Treaty by Nunhems B.V. on Mar. 20, 2015, at the NCIMB Ltd., Ferguson Building, Craibstone Estate, Bucksburn, Aberdeen AB21 9YA, United Kingdom (NCIMB). The deposit has been assigned Accession Number or NCIMB 42390. A deposit of NUN 85931 and of the male and female parent line is also maintained at Nunhems B.V. Access to the deposit will be available during the pendency of this application to persons determined by the Director of the U.S. Patent Office to be entitled thereto upon request. Subject to 37 C.F.R. §1.808(b), all restrictions imposed by the depositor on the availability to the public of the deposited material will be irrevocably removed upon the granting of the patent. The deposit will be maintained for a period of 30 years, or 5 years after the most recent request, or for the enforceable life of the patent whichever is longer, and will be replaced if it ever becomes nonviable during that period. Applicant does not waive any rights granted under this patent on this application or under the Plant Variety Protection Act (7 USC 2321 et seq.).

Although the foregoing invention has been described in some detail by way of illustration and example for purposes of clarity and understanding, it will be obvious that certain changes and modifications may be practiced within the scope of the invention, as limited only by the scope of the appended claims.

All references cited herein are hereby expressly incorporated herein by reference.

EXAMPLES

Development of NUN 85931

The variety NUN 85931 was developed from a male and female proprietary inbred line of Nunhems. The female and male parents were crossed to produce hybrid (F1) seeds of NUN 85931. The seeds of NUN 85931 can be grown to produce hybrid plants and parts thereof (e.g. carrot roots). The hybrid NUN 85931 can be propagated by seeds or vegetatively.

The hybrid variety is uniform and genetically stable. This has been established through evaluation of horticultural characteristics. Several seed production events resulted in no observable deviation in genetic stability. Coupled with the confirmation of genetic stability of the female and male parents the Applicant concluded that NUN 85931 is uniform and stable.

PS 1441 is considered to be the reference variety to NUN 85931. PS 1441 is a commercial variety from Seminis. In Table 1 a comparison between NUN 85931 and PS 1441 is shown based on a trial in the USA. Trial location: El Centro, Calif., USA (coordinates: 32° 44'328"N 115° 22'695"W), elevation 21 feet. Transplant date: Sep. 28, 2013, harvesting date: Feb. 11, 2014.

Two replications of 50 plants each, from which 15 plants or plant parts were randomly selected, were used to measure characteristics. In Table 1 the USDA descriptors of NUN 85931 (this application) and the reference variety (commercial variety) are listed.

In accordance with one aspect of the present invention, there is provided a plant having essentially all physiological and/or morphological characteristics of carrot variety NUN 85931. A description of the physiological and/or morphological characteristics of carrot variety NUN 85931 is presented in Table 1.

Characteristics of NUN 85931

Table 1 shows the USDA descriptors of NUN 85931 and PS 1441 of a field trial in California, US. The values are mean values.

TABLE 1 *

| USDA descriptor | NUN 85931 | PS 1441 |
| --- | --- | --- |
| 1. TYPE | | |
| 1 = Amsterdam; 2 = Flakee; 3 = Berlicum; 4 = Chantenay; 5 = Danvers; 6 = Imperator; 7 = Nantes; 8 = Other (Specify) | 8 (cut&peel) | 8 (cut&peel) |
| 2. REGION OF ADAPTATION IN THE U.S.A.: | | |
| 1 = Northeast; 2 = Northwest; 3 = Southeast; 4 = Southwest; 5 = North Central; 6 = South Central; 7 = Most Regions | 7 | 7 |
| 3. MARKET MATURITY | | |
| No. Days from Seeding to Harvest | 120 | 120 |
| 4. PLANT TOP: (At Harvest Stage) | | |
| Habit: 1 = Erect; 2 = Semi-erect; 3 = Prostrate | 2 | 2 |
| Plant Top Height (from Shoulder to Top of Crown) | 42.3 cm | 35.8 cm |

TABLE 1 *-continued

| USDA descriptor | NUN 85931 | PS 1441 |
| --- | --- | --- |
| Plant Top Neck Diameter | 10.5 mm | 9.0 mm |
| Top Attachment: 1 = Single 2 = Multiple | 1 | 1 |
| 5. LEAF: (At Harvest Stage) | | |
| Name of Color Chart: RHS Colour Cart Blade Color: 1 = Light Green; 2 = Medium Green; 3 = Dark Green; 4 = Other (Specify) | 2 | 2 |
| Color Chart Value | Green 137B | Green 137B |
| Blade Divisions: 1 = Fine; 2 = Medium; 3 = Coarse | 2 | 1 |
| Blade Length (Without Petiole) | 17.8 cm | 16.8 cm |
| Petiole Length from Crown to First Pinna | 25.0 cm | 18.8 cm |
| Petiole Anthocyanin: 1 = Absent; 2 = Present | 1 | 1 |
| Petiole Pubescence: 1 = Absent; 2 = Present | 2 | 1 |
| 6. ROOT: (At Market Maturity) | | |
| Cortex Thickness (Midpoint X-Section) | 6.6 mm | 6.9 mm |
| Core Thickness (Midpoint X-Section) | 6.4 mm | 6.6 mm |
| Carrot Length (Minus Taproot) | 33.9 cm | 26.9 cm |
| Length of Taproot | 53.6 mm | 47.6 mm |
| Diameter at Shoulder | 24.3 mm | 22.9 mm |
| Diameter at Midpoint | 19.7 mm | 21.3 mm |
| Amount Exposed (Above Ground): 1 = None; 2 = 1-10%; 3 = 11-20%; 4 = 21-30%; 5 = 31-40%; 6 = >40% | 1 | 1 |
| Shape: 1 = Round; 2 = Conic; 3 = Cylindrical | 2 | 2 |
| Collar: 1 = Sunken; 2 = Level; 3 = Square | 2 | 2 |
| Shoulder: 1 = Rounded; 2 = Sloping; 3 = Square | 1 | 1 |
| Base: 1 = Pointed; 2 = Medium; 3 = Blunt | 1 | 1 |
| Surface Smoothness: 1 = Very Smooth; 2 = Dimpled or Corrugated | 1 | 1 |
| Number of Secondary Root Scars: 1 = None; 2 = Few; 3 = Many | 1 | 2 |
| Appearance of Secondary Root Scars: 1 = Not Prominent; 2 = Prominent | 1 | 2 |
| Halo: 1 = None; 2 = Faint; 3 = Prominent | 1 | 1 |
| Zoning: 1 = None; 2 = Faint; 3 = Prominent | 2 | 2 |
| Flavor Harshness: 1 = Very Harsh; 2 = Moderately Harsh; 3 = Mildly Harsh | 3 | 3 |
| Flavor Sweetness: 1 = Not Sweet; 2 = Moderately Sweet; 3 = Very Sweet | 2 | 2 |
| COLORS: | | |
| Color choices: 1 = white; 2 = yellow; 3 = orange; 4 = red; 5 = green; 7 = salmon; 8 = light; 9 = dark; 10 = other; color examples: 02 = yellow; 34 = orange-red; 94 = dark red Name of Color Chart: RHS Colour Chart Below Ground Exterior Color | | |
| Shoulder | 03: Greyed-orange 170A | 03: Greyed-orange 170B |
| Skin | 03: Greyed-orange 170A | 03: Greyed-orange 170B |
| X-Section Interior Color | | |
| Core | 03: Greyed-orange 170B | 03: Greyed-orange 170A |
| Phloem | 03: Orange 28B | 03: Orange 28B |
| 7. FLOWER | | |
| Flower color | 01 | 01 |
| Male Fertility | Male-sterile | Male Sterile |

TABLE 1 *-continued

| USDA descriptor | NUN 85931 | PS 1441 |
|---|---|---|
| Anthers | Petaloid | Petaloid |
| 7. SEED | — | — |
| 8. DISEASE REACTIONS: (1 = Susceptible; 2 = Resistant; give races if known) | — | — |
| *Alternaria* Blight | 1 | 1 |
| *Aster* Yellows | 1 | 1 |
| Cavity Spot | 1 | 1 |
| *Cercospora* Blight | 1 | 1 |
| Motley Dwarf Virus | 1 | 1 |
| Powdery Mildew | 1 | 1 |
| *Pythium* Root Dieback | 1 | 1 |
| *Schlerotinia* Decay | 1 | 1 |
| 9. INSECT REACTIONS: (1 = Susceptible; 2 = Resistant; give races if known) | — | — |
| Root Knot Nematode | 1 | 1 |
| 10. PHYSIOLOGICAL REACTIONS; (1 = Susceptible and 2 = Resistant) | — | — |
| Bolting | 2 | 2 |
| Root Splitting | 2 | 2 |

* These are typical values. Values may vary due to environment. Other values that are substantially equivalent are also within the scope of the invention.
— = not measured

CITED REFERENCES

USDA Exhibit C on the world wide web at ams.usda.gov/AMSv1.0/getfile?dDocName=STELDEV3002673
UPOV: on the world wide web at upov.int/edocs/tgdocs/en/tg049.pdf
Simon et al. 2008, Chapter "Carrot" pp 327-357; in the book "Vegetables II—Handbook of Plant Breeding Volume 2, 2008; ISBN 978-0-387-74108-6
Rafal Baranski (2008): Transgenic Plant Journal 2008 (2)1: 18-38.
WO2008/107097
EP 534 858

What is claimed is:

1. A seed of variety NUN 85931, a representative sample of seed of said variety having been deposited under NCIMB Accession Number 42390.

2. A plant, or a part thereof, produced by growing the seed of claim 1.

3. The part of the plant of claim 2, wherein the part is a seed, leaf, pollen, taproot, root, an ovule, or a cell.

4. The plant part of claim 2, wherein the part is a root.

5. A carrot plant, or a part thereof, having all of the physiological and morphological characteristics of the carrot plant of claim 2 when grown under the same conditions.

6. A tissue or cell culture of regenerable cells of the plant of claim 2.

7. The tissue or cell culture according to claim 6, comprising tissues or cells from a plant part selected from the group consisting of embryos, protoplast, meristems, nodes, petioles, cuttings, cotyledons, pollen, leaves, anthers, roots, root tips, taproots, pistils, flowers, seed, stalk and stem.

8. A carrot plant regenerated from the tissue or cell culture of claim 6, having all of the physiological and morphological characteristics of the plant of claim 2 when grown under the same conditions.

9. The carrot plant of claim 8, having all the morphological and physiological characteristics of NUN 85931, a representative sample of seed of said variety having been deposited under NCIMB Accession Number 42390, when grown under the same conditions.

10. A method of vegetatively propagating the plant of claim 2 comprising the steps of:
  a. collecting tissue or cells capable of being propagated from a plant according to claim 2;
  b. cultivating said tissue or cells of (a) to obtain proliferated shoots; and
  c. rooting said proliferated shoots to obtain rooted plantlets, or
  d. cultivating said tissue or cells of (a) to obtain roots; and
  e. cultivating said tissue or cells to obtain proliferated shoots, to obtain plantlets, and optionally
  f. growing plants from said rooted plantlets.

11. A method of producing a carrot plant, comprising crossing the plant of claim 2 with a second carrot plant one or more times, and selecting progeny from said crossing.

12. A method of producing a carrot plant comprising an added desired trait, the method comprising introducing a transgene conferring the desired trait into a plant of carrot variety NUN 85931, a representative sample of seed of said variety having been deposited under NCIMB Accession Number 42390.

13. A method of determining the genotype of the carrot plant of claim 2 comprising obtaining a sample of nucleic acids from said plant and detecting in said nucleic acids a plurality of polymorphisms.

14. The method of claim 13, further comprising the step of storing the results of detecting the plurality of polymorphisms on a computer readable medium.

15. A method for producing a seed of a variety derived from NUN 85931 comprising the steps of:
  a. crossing a carrot plant of variety NUN 85931 with a second carrot plant; and
  b. allowing seed of a variety NUN 85931-derived carrot plant to form, a representative sample of seed of NUN 85931 having been deposited under NCIMB Accession Number 42390.

16. The method of claim 15 further comprising the steps of:
  c. crossing a plant grown from said variety NUN 85931-derived carrot seed with itself or a second carrot plant to yield additional variety NUN 85931-derived carrot seed;
  d. growing said additional variety NUN 85931-derived carrot seed of step (c) to yield additional variety NUN 85931-derived carrot plants; and optionally
  e. repeating the crossing and growing steps of (c) and (d) to generate further variety NUN 85931-derived carrot plants.

17. The method of claim 15, wherein the second carrot plant is of an inbred carrot variety.

18. A method of producing a carrot root comprising:
  (a) obtaining a plant according to claim 2, wherein the plant has been cultivated to maturity; and
  (b) collecting the carrot root from the plant.

19. A food or feed product comprising a carrot root, or parts thereof, of claim 4.

20. A package comprising the seed of claim 1.

21. A container comprising the carrot root of claim 4.

* * * * *